United States Patent
Mendelsohn et al.

(10) Patent No.: US 11,021,576 B2
(45) Date of Patent: *Jun. 1, 2021

(54) POLYMERIC STABILIZING FORMULATIONS

(71) Applicant: Nano Precision Medical, Inc., Emeryville, CA (US)

(72) Inventors: Adam Mendelsohn, Emeryville, CA (US); Au Duong, Emeryville, CA (US); Kathleen Fischer, Emeryville, CA (US); Wouter Roorda, Emeryville, CA (US)

(73) Assignee: Nano Precision Medical, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/600,249

(22) Filed: Oct. 11, 2019

(65) Prior Publication Data

US 2020/0040140 A1     Feb. 6, 2020

Related U.S. Application Data

(63) Continuation of application No. 15/508,572, filed as application No. PCT/US2015/048677 on Sep. 4, 2015, now Pat. No. 10,479,868.

(60) Provisional application No. 62/045,834, filed on Sep. 4, 2014.

(51) Int. Cl.
| | | |
|---|---|---|
| *A61K 31/7088* | (2006.01) |
| *C08G 83/00* | (2006.01) |
| *A61K 38/26* | (2006.01) |
| *A61K 31/541* | (2006.01) |
| *A61K 47/60* | (2017.01) |
| *A61K 9/00* | (2006.01) |
| *A61K 38/02* | (2006.01) |
| *A61K 38/20* | (2006.01) |
| *A61K 38/22* | (2006.01) |

(52) U.S. Cl.
CPC .......... *C08G 83/003* (2013.01); *A61K 9/0024* (2013.01); *A61K 31/541* (2013.01); *A61K 38/26* (2013.01); *A61K 47/60* (2017.08); *A61K 38/02* (2013.01); *A61K 38/208* (2013.01); *A61K 38/22* (2013.01)

(58) Field of Classification Search
None
See application file for complete search history.

(56) References Cited

U.S. PATENT DOCUMENTS

| | | |
|---|---|---|
| 4,694,084 A | 9/1987 | Tomalia et al. |
| 6,190,650 B1 | 2/2001 | Matthews et al. |
| 6,902,744 B1 | 6/2005 | Kolterman et al. |
| 7,955,614 B2 | 6/2011 | Martin et al. |
| 9,511,212 B2 | 12/2016 | Roorda |
| 9,770,412 B2 | 9/2017 | Mendelsohn et al. |
| 9,814,867 B2 | 11/2017 | Mendelsohn et al. |
| 10,045,943 B2 | 8/2018 | Roorda |
| 10,479,868 B2 | 11/2019 | Mendelsohn et al. |
| 2005/0147581 A1 | 7/2005 | Zamiri et al. |
| 2008/0260840 A1 | 10/2008 | Alessi et al. |
| 2011/0311621 A1 | 12/2011 | Salama et al. |
| 2012/0029062 A1 | 2/2012 | Gunaratne et al. |

FOREIGN PATENT DOCUMENTS

| | | | |
|---|---|---|---|
| WO | 2013/085951 A1 | 6/2013 | |
| WO | WO-2013085951 A1 * | 6/2013 | ............. B82Y 30/00 |
| WO | 2016/037128 A1 | 3/2016 | |

* cited by examiner

*Primary Examiner* — Brian Gulledge
(74) *Attorney, Agent, or Firm* — Kilpatrick Townsend & Stockton LLP

(57) ABSTRACT

The present invention provides compositions of a therapeutic agent and a polymeric stabilizing agent for stabilizing the reservoir of an implantable drug delivery system. The present invention also includes an implantable drug delivery system incorporating the composition of the present invention, as well as methods of treating diabetes using the compositions and implantable drug delivery system of the present invention.

29 Claims, 2 Drawing Sheets

POLYMERIC STABILIZING FORMULATIONS

CROSS-REFERENCES TO RELATED APPLICATIONS

The present application is a continuation of U.S. patent application Ser. No. 15/508,572, filed Mar. 3, 2017, allowed, which application is a 371 national stage application of International Application No. PCT/US2015/048677, filed Sep. 4, 2015, which application claims priority to U.S. Provisional Application No. 62/045,834, filed Sep. 4, 2014, the disclosures of which are hereby incorporated by reference in their entireties for all purposes.

BACKGROUND OF THE INVENTION

Current injectable drug delivery therapies can have debilitating side effects which significantly decrease quality of life for patients, or can result in fluctuating blood level of the drug, associated with less than optimal therapeutic efficacy. Additionally, these medications often have to be injected frequently, reducing quality of life for patients, and potentially jeopardizing compliance. As an example, exenatide, a 39 amino acid polypeptide is used for the treatment of diabetes. Current therapies require bi-daily or weekly injections. Ideally, a delivery system could be developed that reduces the injection frequency to much lower levels, such as every 3 or 6 months, or even a year.

Recent advances in implantable nanoporous membranes have produced a novel method to control the release of therapeutics, eliminating the concentration spike associated with an injection. Furthermore, subcutaneously implanted devices can increase patient compliance, thereby increasing treatment efficacy while simultaneously reducing side effects. There is a need for more efficacious formulation of protein and peptide drugs to be used in these implantable devices. The present invention meets this and other needs.

BRIEF SUMMARY OF THE INVENTION

In some embodiments, the present invention provides a pharmaceutical composition having a therapeutic agent, and a polymeric stabilizing agent comprising a polymer and a plurality of stabilizing groups.

In some embodiments, the present invention provides an implantable drug delivery system having a capsule suitable for implantation. The implantable drug delivery system can also have a reservoir encapsulated by the capsule, wherein the reservoir contains a pharmaceutical composition of the present invention containing a therapeutic agent and a polymer functionalized with a plurality of stabilizing groups. The implantable drug delivery system can also have a membrane in contact with the reservoir, wherein the membrane is the only pathway out of the reservoir for the therapeutic agent, and wherein the polymer does not substantially diffuse through the membrane.

In some embodiments, the present invention provides a method of treating a disease in a subject in need thereof, the method including administering to the subject a therapeutically effective amount of a therapeutic agent via an implantable drug delivery system of the present invention containing a pharmaceutical composition of the present invention including the therapeutic agent and a polymer functionalized with a plurality of stabilizing groups, thereby treating the disease.

DETAILED DESCRIPTION OF THE INVENTION

I. General

Figure 1:
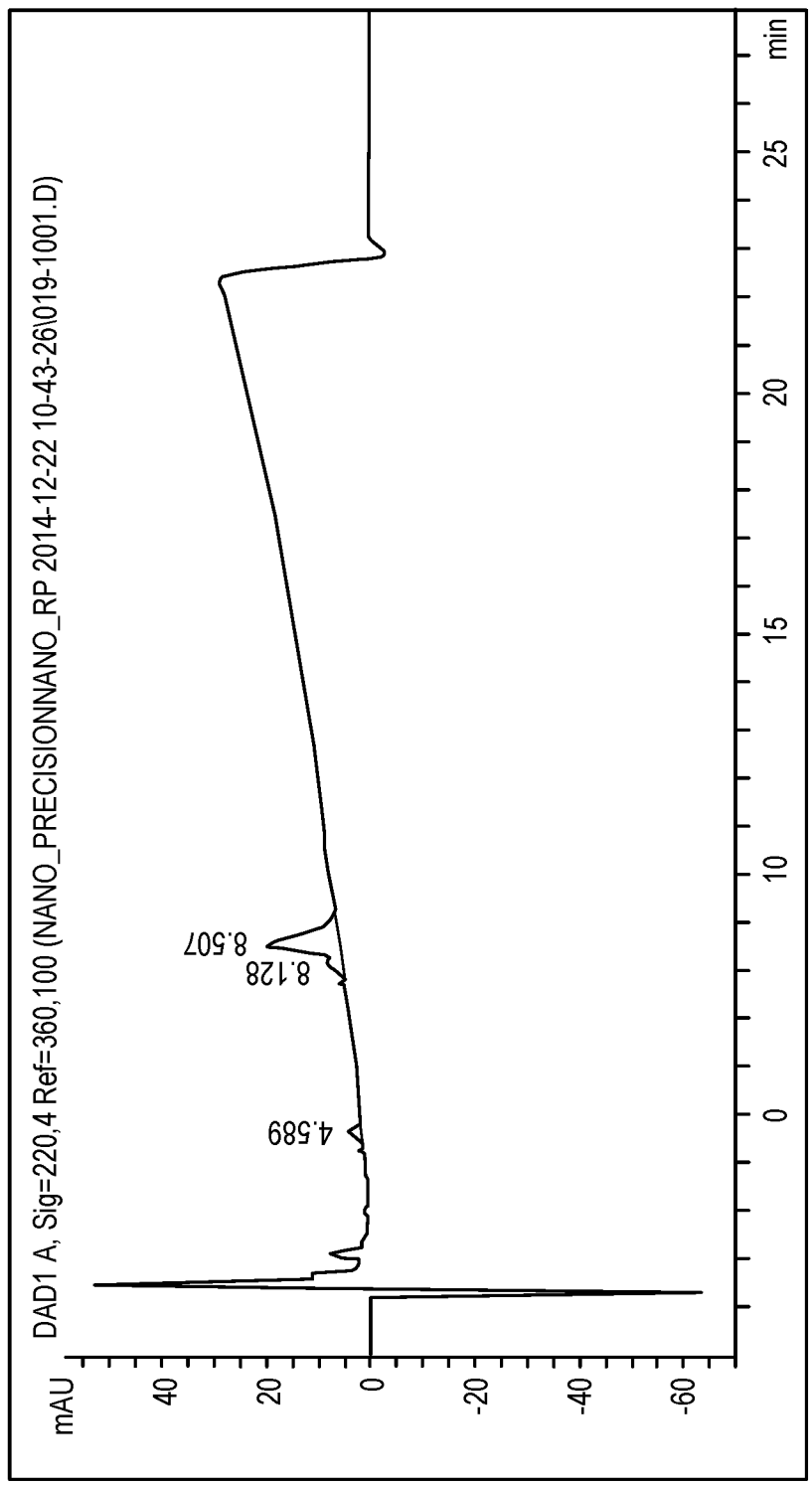
FIG. 1 shows the stability of exenatide in the compositions of the present invention without PAMAM-COOH.
Figure 2:
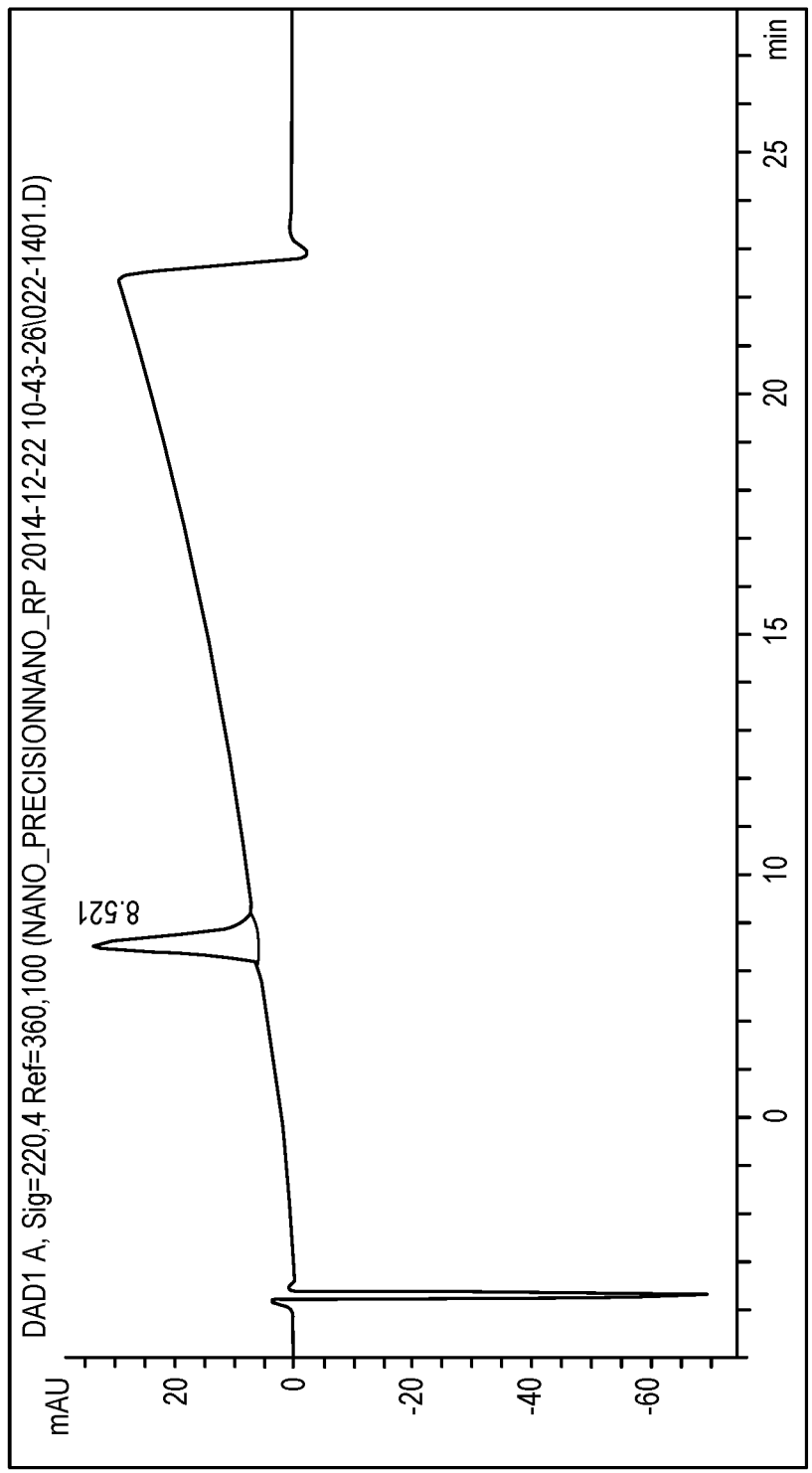
FIG. 2 shows the stability of exenatide in the compositions of the present invention with PAMAM-COOH.

The present invention provides compositions, specifically polymers, that act as a stabilizing agent in the reservoir of an implantable drug delivery system. The buffered environment in the reservoir of the implantable drug delivery system can help stabilize the therapeutic agent delivered from the device. For example, the polymeric stabilizing agent can be a polymeric buffering agent which can include any number of acid groups or base groups to buffer the composition in the reservoir of the device. The preferred pH of the composition can depend on the therapeutic agent in the reservoir, and be acidic or basic. The present invention also includes an implantable drug delivery system incorporating the composition of the present invention, as well as methods of treating diabetes using the compositions and implantable drug delivery system of the present invention.

II. Definitions

"Therapeutic agent" refers to any agent capable of providing a therapeutic response, such as a drug or biologic.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

"Membrane" refers to a substrate allowing diffusion of molecules from one side of the membrane to the other through the membrane.

"Titania nanotube membrane" refers to an array of titania nanotubes on a titanium substrate where at least a portion of the titania nanotubes are open at both ends and capable of allowing diffusion of liquids or solids from one side of the membrane to the other through the titania nanotubes.

"Fluid contact" refers to the contents of the reservoir being able to be released or diffuse from the reservoir to the titania nanotubes. The contents of the reservoir can be in liquid form, but can also be in powder or solid form.

"Aspect ratio" refers to the ratio of length to diameter of the titania nanotubes, including the internal and external diameter.

"Zero-order rate of release" refers to the rate of release that is independent of concentration of the therapeutic agent in the reservoir.

"Treat," "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing or retarding the onset of the symptom. The treatment or amelioration of symptoms can be based on any objective or subjective parameter; including, e.g., the result of a physical examination.

"Subject" refers to animals such as mammals, including, but not limited to, primates (e.g., humans), cows, sheep, goats, horses, dogs, cats, rabbits, rats, mice and the like. In certain embodiments, the subject is a human.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

"Diabetes" or "diabetes mellitus" refers to the group of metabolic diseases having raised blood sugar levels for an extended period of time. Diabetes includes type 1 diabetes, resulting from a lack of insulin production, and type 2 diabetes, which results from insulin resistance where the cells no longer respond to insulin and can progress to a lack of insulin. Other forms of diabetes are known to one of skill in the art.

"Polymeric buffering agent" refers to a polymer having suitable ionizable groups such as acid or base functional groups to buffer a mixture. "Polymer" refers to a macromolecule comprising at least one series of monomer groups. The monomers include, but are not limited to, acrylates, methacrylates, acrylamides, methacrylamides, styrenes, vinyl-pyridine, vinyl-pyrrolidone and vinyl esters such as vinyl acetate. The polymer can adopt a variety of architectures, such as linear, branched, hyperbranched, star, dendritic, cross-linked, comb, etc. The polymer can include a variety of different monomer units in any suitable configuration. For example, linear polymers from at least two different monomers can form block copolymers or random copolymers.

"Acid" refers to a compound that is capable of donating a proton ($H^+$) under the Bronsted-Lowry definition, or is an electron pair acceptor under the Lewis definition. Acids useful in the present invention are Bronsted-Lowry acids that include, but are not limited to, alkanoic acids or carboxylic acids (formic acid, acetic acid, citric acid, lactic acid, oxalic acid, etc.), sulfonic acids and mineral acids, as defined herein. Mineral acids are inorganic acids such as hydrogen halides (hydrofluoric acid, hydrochloric acid, hydrobromice acid, etc.), halogen oxoacids (hypochlorous acid, perchloric acid, etc.), as well as sulfuric acid, nitric acid, phosphoric acid, chromic acid and boric acid. Sulfonic acids include methanesulfonic acid, benzenesulfonic acid, p-toluenesulfonic acid, triflouromethanesulfonic acid, among others.

"Base" refers to a compound capable of accepting a proton ($H^+$) under the Bronsted-Lowry definition, or is an electron pair donor under the Lewis definition. Representative bases include, but are not limited to, hydroxy, alkylhydroxy, amines (—NRR), alkylamine, arylamine, amide (—C(O)NRR), sulfonamide (—S(O)$_2$NRR), phosphonamide (—P(O)(—NRR)$_2$), carboxylate (—C(O)O$^-$), and others.

"Molecular diameter" refers to the diameter of the sphere of gyration of a polymer, which is a physical measure of the size of a molecule, and is defined as two times the mass weighted average distance from the core of a molecule to each mass element in the molecule. Stokes diameter or hydrodynamic diameter reflects the dimension of a molecule plus its associated water molecules as it moves through an aqueous solution, and is defined as the radius of an equivalent hard sphere diffusing at the same rate as the molecule under observation.

"Poly(amidoamine) dendrimer" or "PAMAM dendrimer" refers to a dendrimer having amidoamine branching units. Dendrimers also include a single core, and a plurality of surface groups. Dendrimers can be referred to by the "Generation," which describes the number of branching points between the core and the surface groups, where a Generation 1 PAMAM dendrimer has four amido groups linked to an ethylenediamine core. A Generation 2 PAMAM dendrimer has 8 amido groups linked to the 4 amino surface groups of the Generation 1 PAMAM dendrimer. A Generation 3 PAMAM dendrimer then has 16 surface amino groups, a Generation 4 has 32 surface amino groups, and so on. Different cores can result in different numbers of surface groups at each generation. For example, using a core such as trisaminomethyl results in 6 surface amines for Generation 1, then 12 surface amines for Generation 2, 24 surface amines for Generation 3, and so on.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkylhydroxy" or "hydroxyalkyl" refers to an alkyl group, as defined above, where at least one of the hydrogen atoms is replaced with a hydroxy group. As for the alkyl group, alkylhydroxy groups can have any suitable number of carbon atoms, such as $C_{1-6}$. Exemplary alkylhydroxy groups include, but are not limited to, hydroxy-methyl, hydroxy-ethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Amidoethanol" refers to the group having the structure "—C(O)NH—CH$_2$CH$_2$OH".

"Amidoethylethanol" refers to the group having the structure "—C(O)NH—CH$_2$CH$_2$—NH—CH$_2$CH$_2$OH".

"Amine" refers to the group having the structure "—NH$_2$". Other amines include aminoalkyl, where alkyl is defined as above. When the hydrogens are replaced with other groups, the amine can be a secondary amine or tertiary amine. Quaternary amines are those having four groups linked to the nitrogen atom, "—NR$_3^+$".

"Ethylendieamine" refers to the group having the structure "—NH—CH$_2$CH$_2$—NH—".

"Sodium carboxylate" refers to the group having the structure "—C(O)O$^-$Na$^+$".

"Succinamic acid" refers to the group having the structure "—C(O)NH—C(O)—CH$_2$CH$_2$—C(O)OH".

"Trialkoxysilyl" refers to the group having the structure "—C(O)—CH$_2$CH$_2$—C(O)O—CH$_2$CH$_2$CH$_2$—Si(OAlkyl$_3$)$_3$". Trialkoxysilyl includes any suitable alkoxy group as described above.

"Tris(hydroxymethyl)amidomethane" refers to the group have the structure "—C(O)NH—C(CH$_2$OH)$_3$".

"3-carbomethoxypyrrolidinone" refers to the group having the structure:

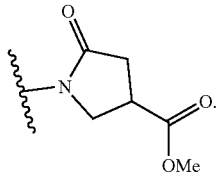 [SMILES: *N1CC(C(=O)OC)CC1=O]

"Consisting of" is a transitional claim term that excludes any element, step or component not specified in the claim.

"Consisting essentially of" is a transitional claim term that limits the scope of a claim to the specified elements, steps or components, and those that do not materially affect the basic and novel characteristic(s) of the claimed invention. "Consisting essentially of" is between the closed claims written in a "consisting of" format and the fully open claims drafted in a "comprising" format.

III. Macro-Stabilizer Compositions

The present invention provides a composition for stabilizing a therapeutic agent by combining the therapeutic agent with a polymer stabilizing group. The polymer stabilizing group can be any suitable stabilizing group, such as a buffering group. For example, the present invention provides a composition containing a therapeutic agent and a polymeric buffering agent capable of buffering an environment to stabilize the therapeutic agent at a particular pH or range of pH values. The buffering agent can be any suitable material, such as a polymer, hydrogel, or other material, that provides the properties of a buffer. In some embodiments, the present invention provides a pharmaceutical composition having a therapeutic agent, and a polymeric stabilizing agent comprising a polymer and a plurality of stabilizing groups. In some embodiments, the present invention provides a pharmaceutical composition having a therapeutic agent, and a polymeric buffering agent comprising a polymer including ionizable groups such as a plurality of acid groups or a plurality of base groups.

Any suitable therapeutic agent can be used in the compositions of the present invention, and are described in greater detail below. In some embodiments, the therapeutic agent can be a peptide, a polypeptide or a protein. In some embodiments, the therapeutic agent can be a peptide. In some embodiments, the therapeutic agent can be beta-glucocerobrosidase, interferon alpha, interferon beta, agasidase alpha, agasidase beta, exenatide, nutropin/somatropin, factor VIII, fondaparinux, aldesleukinand, risperidone, forigerimod, NP fusion proteins, IL-12, a melanocyte stimulating hormone, or bapineuzumab. In some embodiments, the therrapeutic agent can be exenatide, octreotide or fluphenazine. In some embodiments, the therapeutic agent can be exenatide.

In some embodiments, the stabilizing excipient has an oligomeric or polymeric molecular backbone structure. The oligomeric or polymeric backbones may be based on homopolymeric or copolymeric structures. The molecules can have any suitable architecture, including, but not limited to, linear, branched, comb, star, hyperbranched, cross-linked and dendritic architectures. Architectures that adopt a more spherical or globular shape can have certain advantages, and can include branched, comb, star, hyperbranched and dendritic polymers. In some embodiments the molecular structure is a cross-linked structure.

The polymeric buffering agent can include any suitable polymer. Acidic polymers useful for the invention include polyacids based on carboxylic acid groups, like polyacrylic acid and polymethacrylic acid, on sulfonic acids groups like polystyrene sulfonic acid and polyvinyl sulfonic acid, and on phosphonic acid groups, like polyvinyl phosphonic acid and polystyrene phosphonic acid. Basic polymers useful for the invention are often based on amine structures, including primary, secondary, tertiary and quaternary amines. Examples are polyvinyl amine and polystyrene amine and their secondary, tertiary and quaternary derivatives. Other polymers useful as the biocompatible support can include, but are not limited to, polyphosphazenes, polyanhydrides, polyacetals, poly(ortho esters), polyphosphoesters, polycaprolactones, polyurethanes, polylactides, polycarbonates, polyamides, and polyethers, and blends/composites/copolymers thereof. Representative polyethers include, but are not limited to, Poly(ethylene glycol) (PEG), poly(propylene glycol) (PPG), triblock Pluronic ([PEG]n-[PPG]m-[PEG]n), PEG diacrylate (PEGDA) and PEG dimethacrylate (PEGDMA). Other polymers useful in the present invention include, but are not limited to, poly(ethylene glycol), polystyrene, poly(amidoamine) dendrimers, and others. The polymers can have any suitable architecture, including, but not limited to, linear, branched, comb, star, hyperbranched, cross-linked and dendritic. Architectures that adopt a more spherical or globular shape can have certain advantages, and can include branched, comb, star, hyperbranched and dendritic polymers. In some embodiments, the polymer can be a dendrimeric polymers based on poly-amido-amine structures.

Stabilizing functional groups of a chemical nature analogous to the low molecular weight stabilizing excipients mentioned above may be attached to the backbone structure of the oligomeric or polymeric excipient, in some embodiments the attachment is through a covalent chemical link; in some embodiments the attachment is through a non-covalent link, such as a salt formation or complexation. Typical stabilizing functional groups include acids, bases, buffers, anti-oxidants, anti-aggregation agents, and anti-microbials. In some embodiments, each stabilizing group can independently be an acid group, a base group, an anti-oxidant, an anti-microbial, an anti-biotic, a protein clustering agent, or a protein declustering agent.

The polymer can include any suitable functional group to provide the buffering functionality of the polymeric buffering agent. For example, the polymer can be functionalized with an ionizable group such as an acid group or a base group. In some embodiments, each stabilizing group can independently be an acid group or a base group. Representative acid groups include, but are not limited to, carboxylic acid, peroxy acid, amino acid, sulfonic acid, sulfinic acid, phosphonic acid, phosphinic acid, thiol and phenol. In some embodiments, the acid group can be carboxylic acid, amino acid, thiol, and phenol. In some embodiments, the acid groups can be carboxylic acids. For basic groups, amines, pyridines, guanidine, and the like can be used.

Representative stabilizing acid groups include, but are not limited to, carboxylic acid, peroxy acid, amino acid, sulfonic acid, sulfinic acid, phosphonic acid, phosphinic acid.

Representative stabilizing basic groups include, but are not limited to, primary, secondary, tertiary and quaternary amines. The acidic or basic groups of the polymers described above may serve as a basis for further derivatization of the polymers with other stabilizing end groups. Alternatively, polymers with other reactive groups, such as polyvinyl alcohol, may be used for attachment of stabilizing end group, for instance through esterification of a hydroxyl group on the poly-vinyl alcohol with a carboxylic acid group on a stabilizing moiety.

Alternatively, or additionally, the polymer can be functionalized with other stabilizing end groups, such as anti-oxidants. Anti-oxidants can include natural anti-oxidants, such as carotenoids, vitamin E and vitamin C, and synthetic anti-oxidants, like butylated hydroxytoluene, butylated hydroxyanisol and propyl gallate. The end groups of the polymers can be functionalized many different ways, and most anti-oxidants possess multiple functional groups, leaving one with ordinary skills in the art of synthetic chemistry with a variety of options for chemical coupling reactions between the dendrimer and the anti-oxidants.

Anti-oxidative end groups can be based on natural anti-oxidants, such as carotenoids, vitamin E and vitamin C, and on synthetic anti-oxidants, like butylated hydroxytoluene, butylated hydroxyanisol and propyl gallate.

For instance, an anti-oxidant conjugate may be produced through esterification of an acid group on a polymer with the phenyl hydroxyl group of tocopherol, or through esterification with the terminal hydroxyl group of retinol.

Similarly, end groups of the polymers can be functionalized with molecules that promote or reduce clustering of protein molecules in the formulation. Clustering can typically be promoted by compounds enhancing the internal structure of liquid water, such as many carbohydrates, including poly-saccharides, while declustering is often promoted by compounds breaking up internal water structures, such as surfactants. Suitable surfactants include ionic surfactants such a long chain fatty acid salts, or non-ionic surfactants such as the Tween, Brij and Triton series.

Also, in cases where microbial control is desired, the polymer end groups can be functionalized with antibiotics, for instance beta-lactams or aminoglycosides, or with anti-bacterials like quaternary ammonium ions or silver compounds.

Similarly, esterification with one of the phenyl hydroxyl groups of hexachlorophene may be used to produce a oligomer or polymer with anti-bacterial properties. Also, the polymer acid or base groups can be functionalized with antibiotics, for instance beta-lactams or aminoglycosides, or with anti-bacterial like quaternary ammonium ions or silver compounds.

Representative base groups of the polymeric buffering agent include, but are not limited to, amine, alkylamine, arylamine, amide, hydroxy, hydroxy-amine, cyano, and carboxylate. In some embodiments, the base group can be hydroxy, cyano, amine or carboxylate. In some embodiments, the base group can be carboxylate.

In some embodiments, the polymer can be a dendrimer. Dendrimers are characterized by having a core, monomer branching units, and a plurality of end groups. Any suitable dendrimer can be useful in the compositions of the present invention. Representative dendrimers include, but are not limited to, poly(amidoamine) dendrimers, poly(benzylether) dendrimers, poly(alkylether) dendrimers, etc. Poly(amidoamine) dendrimers are also referred to as PAMAM dendrimers. In some embodiments, the polymer can be a poly(amidoamine) dendrimer.

PAMAM dendrimers are characterized by having an amido-amine monomer branching unit. Any suitable core can be used for the PAMAM dendrimers of the present invention. For example, the core can be an alkylenediamine such as ethylene diamine. Other cores are known to one of skill in the art. The end groups of the PAMAM dendrimers can be any suitable end group. Representative end groups include, but are not limited to, amine, alkylamine, alkyl, alkylhydroxy, carboxylate, etc. In some embodiments, the end groups of the poly(amidoamine) dendrimer include sodium carboxylate.

Dendrimers can be prepared by a variety of methods, such as by step-wise, consecutive addition of monomeric units to a growing polymer backbone. Each additional addition of a set of monomers gives rise to what is referred to as a new "generation." The dendrimers useful in the present invention can be of any suitable generation. For example, the dendrimer can be Generation 1, 2, 3, 4, 5, 6, 7, 8, 9, 10, or greater. The higher generation dendrimers can have larger molecular diameters as compared to lower generation dendrimers, so higher generation dendrimers can be preferred. When the dendrimer is a poly(amidoamine) dendrimer, the dendrimer can be any suitable generation. In some embodiments, the poly(amidoamine) dendrimer can be at least a Generation 3 dendrimer. In some embodiments, the poly(amidoamine) dendrimer can be at least a Generation 5 dendrimer. In some embodiments, the poly(amidoamine) dendrimer can be at least a Generation 7 dendrimer. In some embodiments, the poly(amidoamine) dendrimer can be at least a Generation 9 dendrimer.

The polymers of the present invention can be of any suitable molecular diameter. For example, the polymer can have a molecular diameter of at least 1 nm, or of at least 2, 3, 4, 5, 6, 7, 8, 9, or of at least 10 nm. In some embodiments, the polymer can have a molecular diameter of at least 3 nm. In some embodiments, the polymer can have a molecular diameter of at least 5 nm.

The polymers of the present invention can be obtained via commercial sources or can be prepared by any means known to one of skill in the art.

The table below shows a number of characteristic properties of PAMAM dendrimers of increasing generation, such as those produced by Dendritech Inc., from Midland, Mich.

| Generation | Molecular Weight | Measured Diameter (nm) | Surface Groups |
| --- | --- | --- | --- |
| 0 | 517 | 1.5 | 4 |
| 1 | 1,430 | 2.2 | 8 |
| 2 | 3,256 | 2.9 | 16 |
| 3 | 6,909 | 3.6 | 32 |
| 4 | 14,215 | 4.5 | 64 |
| 5 | 28,826 | 5.4 | 128 |
| 6 | 58,048 | 6.7 | 256 |
| 7 | 116,493 | 8.1 | 512 |
| 8 | 233,383 | 9.7 | 1024 |
| 9 | 467,162 | 11.4 | 2048 |
| 10 | 934,720 | 13.5 | 4096 |

The amino surface groups or end groups of the polymer chains can be used to derivatize the molecule through reactions like amide- or Schiff's base formation. Derivatives produced in this and other manners include amidoethanol-, succinamic acid-, carboxylate-, and hydrophobic end groups. These end groups can be used as a basis for further derivatization.

The pharmaceutical composition of the present invention can have any suitable pH. For example, the pH can be acidic, i.e., less than 7, when the polymeric buffering agent includes acid groups. When the compositions are acidic, the pH of the compositions of the present invention can have a pH of less than 7, or a pH of from about 2 to 7, or from about 3 to 7, or from about 4 to about 6. In some embodiments, the pH of the composition can be less than 7. In some embodiments, the pH of the composition can be from about 3 to 7. In some embodiments, the pH of the composition can be from about 4 to about 6. When the compositions are basic, the pH of the composition can be greater than 7, such as when the polymeric buffering agent includes base groups. The compositions of the present invention can have a pH of greater than 7, or a pH of from 7 to about 12, or from 7 to about 11, or from about 8 to about 10.

In many instances, drug formulations suitable for use in an implantable controlled release drug delivery system require the presence of stabilizing excipients to maintain stability of the drug over the duration of implantation. Typical stabilizing excipients include acids, bases, buffers, anti-aggregation agents (for proteins), anti-oxidants and anti-microbials. Frequently, such stabilizing excipients are low molecular weight compounds. In cases where the drug, also referred to as the Active Pharmaceutical Ingredient (API) is significantly larger than the excipients, and where the pore size of the membrane is tailored towards controlling release of the drug, the low molecular weight excipients may be released too fast. The stability of the active agent can be measured by any suitable means. For example, Example 16 describes a method of determining the stability of the active agent using HPLC, with and without the stabilizing polymer PAMAM-COOH.

In some embodiments, formulations according to the invention comprise a therapeutic agent and a stabilizing excipient, wherein the stabilizing excipient has a molecular dimension in solution that is of the same order of magnitude as a corresponding molecular dimension of the therapeutic agent in the solution. Any appropriate measure of molecular dimension may be used for the comparison, such as radius of gyration, Stokes radius, or, in aqueous solutions, hydrodynamic radius.

In some embodiments the excipient has a molecular dimension in solution at least equal to the size of the molecular dimension of the therapeutic agent in the solution; in preferred embodiments the excipient has a molecular dimension in solution at least 2 times the size of the molecular dimension of the therapeutic agent in the solution; in most preferred embodiments the excipient has a molecular dimension in solution at least 5 times the size of the molecular dimension of the therapeutic agent in the solution.

Solutions in this context may be aqueous, organic, or mixed aqueous organic solutions. By tailoring the molecular dimensions of the excipient molecules to the dimensions of the therapeutic agent, their release may be reduced to levels that are appropriate to maintain sufficient levels of excipient in the formulation for a required period of time. By selecting excipients that are larger than the pore size of the membranes of their delivery systems, their release may be substantially prevented.

In some embodiments, the present invention provides a pharmaceutical composition comprising a therapeutic agent and a polymeric stabilizing agent comprising a polymer and a plurality of stabilizing groups. In some embodiments, the pharmaceutical composition consists essentially of a therapeutic agent and a polymeric stabilizing agent consisting essentially of a polymer and a plurality of stabilizing groups. In some embodiments, the pharmaceutical composition consists of a therapeutic agent and a polymeric stabilizing agent consisting of a polymer and a plurality of stabilizing groups.

In some embodiments, the pharmaceutical composition comprises exenatide and a PAMAM-COOH dendrimer. In some embodiments, the pharmaceutical composition consists essentially of exenatide and a PAMAM-COOH dendrimer. In some embodiments, the pharmaceutical composition consists of exenatide and a PAMAM-COOH dendrimer. In some embodiments, the pharmaceutical composition comprises exenatide, a PAMAM-COOH dendrimer and a PAMAM-methionine dendrimer. In some embodiments, the pharmaceutical composition comprises exenatide, a PAMAM-COOH dendrimer, a PAMAM-methionine dendrimer and a PAMAM-silver sulfadizaine dendrimer. In some embodiments, the pharmaceutical composition comprises exenatide, a PAMAM-COOH dendrimer and a PAMAM-tocopherol dendrimer. In some embodiments, the pharmaceutical composition comprises exenatide, a PAMAM-COOH dendrimer, a PAMAM-tocopherol dendrimer and a PAMAM-sulfur sulfadiazine dendrimer.

In some embodiments, the pharmaceutical composition comprises octreotide, a PAMAM-COOH dendrimer and a PAMAM-methionine dendrimer. In some embodiments, the pharmaceutical composition comprises octreotide, a PAMAM-COOH dendrimer, a PAMAM-methionine dendrimer and a PAMAM-hexachlorophene dendrimer. In some embodiments, the pharmaceutical composition comprises octreotide, a PAMAM-COOH dendrimer and a PAMAM-retinol dendrimer. In some embodiments, the pharmaceutical composition comprises octreotide, a PAMAM-COOH dendrimer, a PAMAM-retinol dendrimer and a PAMAM-sulfur sulfadiazine dendrimer.

In some embodiments, the pharmaceutical composition comprises fluphenazine and a PAMAM-tocopherol dendrimer.

The compositions of the present invention can be prepared by any means known to one of skill in the art.

IV. Therapeutic Agents

The present invention provides compositions and implantable drug delivery systems containing therapeutic agents, and methods of using the therapeutic agents for treating diabetes and for administering to a subject in need of treatment by the therapeutic agent. Any suitable therapeutic agent can be used in the compositions, devices and methods of the present invention.

For example, the therapeutic agent can be a small molecule drug, such as one having a molecular weight of less than about 1000 g/mol, or less than about 750 g/mol, or less than about 500 g/mol. In some embodiments, the therapeutic agent can be tacrine, memantine, rivastigmine, galantamine, donepezil, levetiracetam, repaglinide, atorvastatin, alefacept, tadalafil, vardenafil, sildenafil, fosamprenavir, oseltamivir, valacyclovir and valganciclovir, abarelix, adefovir, alfuzosin, alosetron, amifostine, amiodarone, aminocaproic acid, aminohippurate sodium, aminoglutethimide, aminolevulinic acid, aminosalicylic acid, amlodipine, amsacrine, anagrelide, anastrozole, aprepitant, aripiprazole, asparaginase, atazanavir, atomoxetine, anthracyclines, bexarotene, bicalutamide, bleomycin, bortezomib, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daptomycin, daunorubicin, deferoxamine, dexamethasone, diclofenac, diethylstilbestrol, docetaxel, doxorubicin, dutasteride, eletriptan, emtricitabine, enfuvirtide, eplerenone, epirubicin, estramustine, ethinyl estradiol, etoposide, exemestane, ezetimibe, fentanyl, fexofenadine, fludarabine, fludrocortisone, fluorouracil, fluoxymesterone, flutamide, fluticazone, fondaparinux, fulvestrant, gamma-hydroxybutyrate, gefitinib, gemcitabine, epinephrine, L-Dopa, hydroxyurea, icodextrin, idarubicin, ifosfamide, imatinib, irinotecan, itraconazole, goserelin, laronidase, lansoprazole, letrozole, leucovorin, levamisole, lisinopril, lovothyroxine sodium, lomustine, mechlorethamine, medroxyprogesterone, megestrol, melphalan, memantine, mercaptopurine, mequinol, metaraminol bitartrate, methotrexate, metoclopramide, mexiletine, miglustat, mitomycin, mitotane, mitoxantrone, modafinil, naloxone, naproxen, nevirapine, nicotine, nilutamide, nitazoxanide, nitisinone, norethindrone, octreotide, oxaliplatin, palonosetron, pamidronate, pemetrexed, pergolide, pentostatin, pilcamycin, porfimer, prednisone, procarbazine, prochlorperazine, ondansetron, palonosetron, oxaliplatin, raltitrexed, rosuvastatin, sirolimus, streptozocin, pimecrolimus, sertaconazole, tacrolimus, tamoxifen, tegaserod, temozolomide, teniposide, testosterone, tetrahydrocannabinol, thalidomide, thioguanine, thiotepa, tiotropium, topiramate, topotecan, treprostinil, tretinoin, valdecoxib, celecoxib, rofecoxib, valrubicin, vinblastine, vincristine, vindesine, vinorelbine, voriconazole, dolasetron, granisetron, formoterol, fluticasone, leuprolide, midazolam, alprazolam, amphotericin B, podophylotoxins, nucleoside antivirals, aroyl hydrazones, sumatriptan, eletriptan; macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, gatifloxacin, gemifloxacin, grepafloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including peniclinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, salmeterol, ipratropium bromide, flunisolide, cromolyn sodium, and ergotamine tartrate; taxanes such as paclitaxel; SN-38, or tyrphostines. Therapeutic agents can also be aminohippurate sodium, amphotericin B, doxorubicin, aminocaproic acid, aminolevulinic acid, arninosalicylic acid, metaraminol bitartrate, pamidronate disodium, daunorubicin, levothyroxine sodium, lisinopril, cilastatin sodium, mexiletine, cephalexin, deferoxamine, or amifostine.

Other therapeutic agents useful in the present invention can include peptides, polypeptides, proteins, antibodies, etc. In some embodiments, the therapeutic agent can be erythropoietin, granulocyte colony stimulating factor (G-CSF), GM-CSF, interferon alpha, interferon beta, human growth hormone, imiglucerase, or RANK ligand. In other embodiments, the therapeutic agents can be Aβ, agalsidase, alefacept, alkaline phosphatase, aspariginase, amdoxovir (DAPD), antide, becaplermin, botulinum toxin including types A and B and lower molecular weight compounds with botulinum toxin activity, calcitonins, CD1d, cyanovirin, denileukin diftitox, erythropoietin (EPO), EPO agonists, dornase alpha, erythropoiesis stimulating protein (NESP), coagulation factors such as Factor V, Factor VII, Factor VIIa, Factor VIII, B domain deleted Factor VIII, Factor IX, Factor X, Factor XII, Factor XIII, von Willebrand factor; ceredase, Fc gamma r2b, cerezyme, alpha-glucosidase, N-Acetylgalactosamine-6-sulfate sulfatase, collagen, cyclosporin, alpha defensins, beta defensins, desmopressin, GLP-1 analogs such as exendin-4 (EXENATIDE®), cytokines, cytokine receptors, granulocyte colony stimulating factor (G-CSF), thrombopoietin (TPO), alpha-1 proteinase inhibitor, elcatonin, granulocyte macrophage colony stimulating factor (GM-CSF), fibrinogen, filgrastim, growth hormones human growth hormone (hGH), somatropin, growth hormone releasing hormone (GHRH), GRO-beta, GRO-beta antibody, bone morphogenic proteins such as bone morphogenic protein-2, bone morphogenic protein-6, parathyroid hormone, parathyroid hormone related peptide, OP-1; acidic fibroblast growth factor, basic fibroblast growth factor, Fibroblast Growth Factor 21, CD40 ligand, ICOS, CD28, B7-1, B7-2, TLR and other innate immune receptors, heparin, human serum albumin, low molecular weight heparin (LMWH), interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-17, interleukin-21, interleukin-13 receptor, interleukin-17 receptor; lactoferrin and lactoferrin fragments, luteinizing hormone releasing hormone (LHRH), insulin, pro-insulin, insulin analogues, amylin, C-peptide, somatostatin, somatostatin analogs including octreotide, vasopressin, follicle stimulating hormone (FSH), imiglucerase, influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), trk A, trk B, osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF) (e.g., TNF-α and TNF-β), TNF receptors (e.g., TNF-α receptor and TNF-β receptor), CTLA4, CTLA4 receptor, monocyte chemoattractant protein-1, endothelial growth factors, parathyroid hormone (PTH), PTHrP, glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyribonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-484, CDP-571, CDP-791, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, I$^{131}$tositumomab, trastuzumab, tuvirumab, visilizumab, or fragments or mimetics thereof.

In other embodiments, the therapeutic agent can be a fusion protein. For example, the therapeutic agent can be an immunoglobulin or portion of an immunoglobulin fused to one or more certain useful peptide sequences. The therapeutic agent can also contain an antibody Fc fragment.

In some embodiments, the therapeutic agent can be a human protein or human polypeptide, for example, a heterologously produced human protein or human polypeptide. Numerous proteins and polypeptides are disclosed herein for which there is a corresponding human form (i.e., the protein or peptide is normally produced in human cells in the human body). Examples of human proteins include, without limitation, human antibodies, human enzymes, human hormones and human cytokines such as granulocyte colony stimulation factor, granulocyte macrophage colony stimulation factor, interferons (e.g., alpha interferons and beta interferons), human growth hormone and erythropoietin.

Other examples of therapeutic agents include, without limitation, factor VIII, b-domain deleted factor VIII, factor VIIa, factor IX, factor X, anticoagulants; hirudin, alteplase, tpa, reteplase, tpa, tpa-3 of 5 domains deleted, insulin, insulin lispro, insulin aspart, insulin glargine, long-acting insulin analogs, complement C5, hgh, glucagons, tsh, follitropin-beta, fsh, gm-csf, pdgh, ifn alpha2, ifn alpha2a, ifn alpha2b, inf-aphal, consensus ifn, ifn-beta, ifn-beta 1b, ifn-beta 1a, ifn-gamma (e.g., 1 and 2), ifn-lambda, ifn-delta, il-2, il-11, hbsag, ospa, murine mab directed against t-lymphocyte antigen, murine mab directed against tag-72, tumor-associated glycoprotein, fab fragments derived from chimeric mab directed against platelet surface receptor gpII(b)/III(a), murine mab fragment directed against tumor-associated antigen ca125, lysyl oxidase, LOX2, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, chimeric mab directed against cd 20 surface antigen of b lymphocytes dornase-alpha dnase, beta glucocerebrosidase, tnf-alpha, il-2-diptheria toxin fusion protein, tnfr-lgg fragment fusion protein laronidase, dnaases, alefacept, darbepoetin alpha (colony stimulating factor), tositumomab, murine mab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, etanercept, antidiuretic hormones, prolactin and thyroid stimulating hormone.

Further examples of therapeutic agents include, but are not limited, to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath; Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD2O IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CATI-BASF); CDP870 is a humanized anti-TNF-α Fab fragment (Celltech); IDEC-151 is a primatized anti-CD4 IgG1 antibody (DEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTE-GREN™ is a humanized anti-VLA-4 IgG antibody (Elan); CAT-152, a human anti-TGF-$\beta_2$ antibody (Cambridge Ab Tech); Cetuximab (BMS) is a monoclonal anti-EGF receptor (EGFr) antibody; Bevacizuma (Genentech) is an anti-VEGF human monoclonal antibody; Infliximab (Centocore, JJ) is a chimeric (mouse and human) monoclonal antibody used to treat autoimmune disorders; Gemtuzumab ozogamicin (Wyeth) is a monoclonal antibody used for chemotherapy; and Ranibizumab (Genentech) is a chimeric (mouse and human) monoclonal antibody used to treat macular degeneration.

Other antibodies, such as single domain antibodies are also useful in the present invention. A single domain antibody (sdAb, called Nanobody by Ablynx) is an antibody fragment consisting of a single monomeric variable antibody domain. Like a whole antibody, the sdAb is able to bind selectively to a specific antigen. With a molecular weight of only 12-15 kDa, single domain antibodies are much smaller than common antibodies (150-160 kDa). A single domain antibody is a peptide chain of about 110 amino acids in length, comprising one variable domain (VH) of a heavy chain antibody, or of a common IgG.

In some embodiments, the therapeutic agent can be a peptide, polypeptide, or protein. In some embodiments, the therapeutic agent can be beta-glucocerobrosidase, interferon alpha, interferon beta, agasidase alpha, agasidase beta, exenatide, nutropin/somatropin, factor VIII, fondaparinux, aldesleukinand, risperidone, forigerimod, NP fusion proteins, IL-12, a melanocyte stimulating hormone, or bapineuzumab. In some embodiments, the therapeutic agent can be exenatide.

The therapeutic agent can be administered by any means known to one of skill in the art. For example, the therapeutic agent can be administered via the implantable drug delivery system of the present invention. In some embodiments, the present invention provides a method of administering a therapeutic agent to a subject in need thereof, the method including implanting in the subject an implantable drug delivery system of the present invention containing a pharmaceutical composition of the present invention including the therapeutic agent and a polymeric buffering agent comprising a polymer functionalized with a plurality of acid groups or a plurality of base groups, wherein the therapeutic agent elutes from the implantable drug delivery system, thereby administering the therapeutic agent.

V. Implantable Drug Delivery System

The present invention provides an implantable drug delivery system capable of delivering the therapeutic agent from the device. In some embodiments, the present invention provides an implantable drug delivery system having a capsule suitable for implantation. The implantable drug delivery system can also have a reservoir encapsulated by the capsule, wherein the reservoir contains a pharmaceutical composition of the present invention containing a therapeutic agent and a polymer functionalized with a plurality of stabilizing groups. The implantable drug delivery system can also have a membrane in contact with the reservoir, wherein the membrane is the only diffusion pathway out of the reservoir for the therapeutic agent, and wherein the polymer does not substantially diffuse through the membrane.

The capsule can be any capsule that is biocompatible with the body. The capsule can be prepared from any suitable material such as biocompatible materials, metals, polymers and combinations thereof. Useful metals can be pure metals or alloys, and include, but are not limited to, titanium and steel. Polymers useful in the present invention include any natural or synthetic polymer that is biocompatible with the body. In some embodiments, the capsule includes titanium.

The capsule can have any suitable shape or size. The capsule can be spherical, elliptical, oblong, circular, or cylindrical, among others.

The device also includes the reservoir which contains the therapeutic agent. Any therapeutic agent is useful in the device of the present invention, as described above. The therapeutic agent can be in any suitable form in the reservoir, such as a liquid, a solid or a suspension. Solid forms include, but are not limited to, powders and micronized particles. For example, the powder can be lyophilized.

Any suitable membrane can be used in the implantable drug delivery system of the present invention. For example, the membrane can be prepared from any suitable polymer, metal, metal oxide, ceramic inorganic material, or combination thereof. Suitable materials for the membrane include, but are not limited to, silicon, silica, titanium and titania. In some embodiments, the membrane can be titania. Suitable organic materials include any polymeric system that has adequate permeability for H+ and Na+ ions, and for the therapeutic agent. Particularly suitable may be hydrogel-based membranes, if necessary as composite materials with an embedded reinforcing mesh. The membrane may be based on any of the hydrogels described above, provided they are formulated with adequate physical integrity, for instance by incorporating cross-linkers. Suitable materials include poly-acrylic hydrogels like poly-hydroxymethyl methacrylate, cross-linked with ethyleneglycoldimethacrylate, and poly-urethane hydrogels like those manufactured by reacting hexamethylenediisocyanate trimers with diols like polyethyleneglycol. In some embodiments, the membrane can be a titania nanotube membrane.

In some embodiments the membrane pores have a diameter of the same order of magnitude as the hydrodynamic diameter of dissolved substances, such as a therapeutic agent in the formulation. In some embodiments, the pores have a diameter smaller than hydrodynamic diameter of dissolved substances in the formulation. Because of the finite size of the pores, such membranes may act as a size cut-off filter for dissolved substances in the formulations of the drug delivery systems.

The membranes of the present invention can have any suitable pore size. For example, the membrane pores can have a diameter of at least about 10 μm, 1 μm, 1000 nm, 500 nm, 100 nm, 50 nm, 25, nm, 10, nm at least about 5 nm, or at least about 1 nm. The membrane pores can also have a diameter of from about 1 nm to about 10 μm, or from about 1 nm to about 1 μm, or from about 1 nm to about 500 nm, or from about 1 nm to about 100 nm, or from about 1 nm to about 50 nm.

In some embodiments, the membrane can be a titania nanotube membrane on a titanium substrate, such as that described in PCT Publication No. WO 2013/085951 or U.S. Application Publication No. 2014/0371687. In some embodiments, the pores in the nanotube membranes have diameters in a range of 1-5 times or 1, 2, 3, 4, or 5 times the hydrodynamic radius of the drug molecules diffusing through their aqueous phase. It has been shown that under those conditions drug release rates may be achieved that are independent of the gradient of the concentration of the drug between a reservoir in the drug delivery system and the environment into which the drug is released.

The implantable drug delivery system of the present invention can have one or more membranes. For example, the implantable drug delivery system can have 1, 2, 3, 4, or more membranes. The membranes can have the same or different pore diameters. When the implantable drug delivery system has more than one membrane each with the same pore diameter, each membrane can provide a diffusion pathway for the the therapeutic agent. Alternatively, the membranes can each have different pore diameters such that one or more of the membranes does not provide a diffusion pathway for the therapeutic agent. In some embodiments, when two membranes are present in the implantable drug delivery system, only one membrane provides a diffusion pathway for the therapeutic agent.

In some embodiments, the present invention provides a device having a capsule suitable for implantation. The device also includes a reservoir encapsulated by the capsule, wherein the reservoir is suitable for containing a therapeutic agent. The device also includes a titania nanotube membrane on a titanium substrate, wherein the titanium substrate is attached to the capsule such that the titanium substrate is in contact with the reservoir, wherein the titania nanotube membrane comprises a plurality of titania nanotubes in fluid contact with the reservoir. The device is such that the plurality of titania nanotubes is the only pathway out of the reservoir for the therapeutic agent.

The titania nanotubes are in fluid contact with the reservoir such that the therapeutic agent, whether in liquid, solid or suspension form, can be released from the reservoir and into the titania nanotubes at the titanium substrate, followed by exiting the titania nanotubes at the opposite end and entering the body. The rate of release of the therapeutic agent can be any suitable rate of release, such as zero-order rate of release. In some embodiments, the release of the therapeutic agent from the reservoir and through the titania nanotube membrane is a zero-order rate of release.

The combination of the composition of the present invention and the implantable drug delivery system of the present invention allow the stabilization of the therapeutic agent of the composition in the reservoir of the implantable drug delivery system. For example, the therapeutic agent can be stabilized by implanting in a patient in need thereof, the drug delivery system of the present invention having a composition of the present invention in the reservoir, and maintaining a pH inside the reservoir to form a pH differential of at least 0.5 pH units with the pH of the patient's tissue immediately surrounding the implantable drug delivery system. In some embodiments, the present invention provides a method of stabilizing a therapeutic agent in a reservoir of an implantable drug delivery system, the method comprising implanting in a patient in need thereof, the implantable drug delivery system comprising a reservoir containing a therapeutic agent and a polymer stabilizing agent comprising a plurality of stabilizing groups that can each be an acid group or a base group, and maintaining the pH inside the reservoir to create a pH differential of at least 0.5 pH units with the pH of the patient's tissue surrounding the implantable drug delivery system.

VI. Method of Treating a Disease

The present invention provides a method of treating a disease by administering a therapeutic agent suitable to treat the disease from an implantable drug delivery system of the present invention using a composition of the present invention. The present invention provides a method of treating diabetes by administering a therapeutic agent from an implantable drug delivery system of the present invention using a composition of the present invention. In some embodiments, the present invention provides a method of treating diabetes in a subject in need thereof, the method including administering to the subject a therapeutically effective amount of a therapeutic agent via an implantable drug delivery system of the present invention containing a pharmaceutical composition of the present invention including the therapeutic agent and a polymer functionalized with a plurality of stabilizing groups, thereby treating the diabetes. In some embodiments, the present invention provides a method of treating diabetes in a subject in need thereof, the method including administering to the subject a therapeutically effective amount of a therapeutic agent via an implantable drug delivery system of the present invention containing a pharmaceutical composition of the present invention including the therapeutic agent and a polymer functionalized with a plurality of acid groups or a plurality of base groups, wherein the acid and base groups are not all neutralized during the administering, thereby treating the diabetes.

Any suitable disease can be treated by the method of the present invention. For example, the disease can be diabetes, cancer, neurological disorders, inflammatory diseases, and others. In some embodiments, the disease can be diabetes.

Any suitable therapeutic agent and polymer can be used in the method of the present invention, as described above. In some embodiments, the therapeutic agent can be exenatide.

Any suitable type of diabetes can be treated using the method of the present invention. The term diabetes encompasses several different hyperglycemic indications. These states include Type 1 (insulin-dependent diabetes mellitus or IDDM) and Type 2 (non-insulin dependent diabetes mellitus or NIDDM) diabetes. The hyperglycemia present in individuals with Type 1 diabetes is associated with deficient, reduced, or nonexistent levels of insulin which are insufficient to maintain blood glucose levels within the physiological range. Methods of treatment of Type 1 diabetes involves administration of replacement doses of insulin, generally by a parenteral route.

The hyperglycemia present in individuals with Type 2 diabetes is initially associated with normal or elevated levels of insulin; however, these individuals are unable to maintain metabolic homeostasis due to a state of insulin resistance in peripheral tissues and liver and, as the disease advances, due to a progressive deterioration of the pancreatic β-cells which are responsible for the secretion of insulin. In some embodiments, the diabetes can be type 2 diabetes. In some embodiments, the diabetes can be type 1 diabetes. In some embodiments, the disease can be type 2 diabetes. In some embodiments, the disease can be type 1 diabetes.

Any suitable subject can be treated using the method of the present invention. In some embodiments, the subject can be a human.

The therapeutic agent can be delivered in any therapeutically effective amount. The therapeutic agent of the present invention can be delivered in any suitable amount, and can depend on various factors including, but not limited to, weight and age of the subject, state of the disease, etc. Suitable dosage ranges for the compound of the present invention include from about 0.1 µg to about 10,000 µg or about 1 µg to about 1000 µg or about 10 µg to about 750 or about 25 µg to about 500 µg or about 50 µg to about 250 µg. Suitable dosages for the compound of the present invention include about 1 µg, 5, 10, 20, 30, 40, 50, 60, 70, 80, 90, 100, 200, 300, 400, 500, 600, 700, 800, 900 or 1000 µg.

The doses suitable for the treatment of diabetes can provide any suitable mean steady-state plasma concentration of the therapeutic agent in the subject. For example, the mean steady state plasma concentration can be from 10 pg/ml to 10,000 ng/ml. In some embodiments, the mean steady state plasma concentration for exenatide can be from 170 pg/ml to 600 pg/ml. In some embodiments, the mean steady state plasma concentration for exenatide can be from 170 pg/ml to 350 pg/ml. In some embodiments, the mean steady state plasma concentration for exenatide can be from 170 pg/ml to 290 pg/ml.

In certain embodiments, the exenatide concentration is sufficient to achieve an average or minimum circulating blood plasma level of exenatide of at least about 50 pg/ml for a period of at least about 12 hours, at least about 1 day, at least about 2 days, at least about 3 days, at least about 1 week, at least about 2 weeks, at least about 3 weeks, at least about 1 month, at least about 3 months, or at least about 6 months or even more.

VII. Examples

General. Below are examples of substances based on a Poly-Amido-Amine dendritic backbone structure, that are suitable for use in formulations of the invention.
1. PAMAM-$NH_2$ (PAMAM)
2. PAMAM-COOH (PAMAM carboxylic acid)
3. PAMAM-NH—CO—$CH_2$—$CH_2$—COOH (PAMAM succinic acid)
4. PAMAM-CO—NH—$CH_2$—$CH_2$—OH (PAMAM amidoethanol)
5. PAMAM-Tocopherol
6. PAMAM-Retinol
7. PAMAM-BHT
8. PAMAM-Methionine
9. PAMAM-Maltose
10. PAMAM-Silver Sulfadiazine
11. PAMAM-hexachlorophene
12. PAMAM-Streptomycin Polymers 1, 2, 3 and 4 are commercially available, for instance from Dendritech, Inc. in Midland, Mich. Polymer 5 can be prepared by esterification of Polymer 2 with the phenyl hydroxyl group of tocopherol. Polymer 6 can be prepared by esterification of Polymer 3 with the terminal hydroxyl group of retinol. Polymer 7 can be prepared by esterification of Polymer 2 with the phenyl hydroxyl group of BHT. Preparation of Polymer 6 and Polymer 7 can proceed via Fischer esterification under conditions of water removal, for instance with molecular sieves or under azeotropic distillation, with catalytic amounts of an acid like p-toluenesulfonic acid. Polymer 8 can be prepared by amide bond formation between the COOH group of methionine with the $NH_2$ group from Polymer 1, such as by using a carbodiimide reagent. Polymer 9 can be prepared by formation of a Schiff's base between the aldehyde form of maltose and the $NH_2$ group from Polymer 1, followed by a reduction with sodium borohydride. Polymer 10 can be prepared similarly to Polymer 8, by reacting the phenyl $NH_2$ group of silver sulfadiazine with the COOH group of Polymer 3. Polymer 11 can be prepared similarly to Polymer 6, by esterification of the phenyl hydroxy of hexachlorophene with the acid group of Polymer 2. Polymer 12 can also be prepared via esterification similarly to Polymer 6, such as by reaction of Polymer 2 or Polymer 3 with a hydroxy on the streptomycin molecule, or by preparing an amide under conditions similar for preparation of Polymer 8.

Active agents include the following:
Exenatide, a peptide molecule, is sensitive to oxidation, as well as to degradation at pH levels above 6.

Octreotide, a peptide molecule, is sensitive to oxidation and is preferably kept at a pH between 4 and 4.5.

Fluphenazine is a low molecular weight anti-psychotic with a phenothiazine group that is prone to oxidation. It has limited water solubility.

Example 1. Composition

Exenatide, 10 is admixed with 10 mg of a Generation 5 PAMAM dendrimer with sodium carboxylate end groups and an ethylenediamine core.

Example 2. Treating Diabetes

A 50 year-old male, weighing 175 pounds, presents to a physician with type 2 diabetes. The physician implants in the patient the drug delivery system described above containing exenatide and a Generation 5 PAMAM dendrimer with sodium carboxylate end groups and an ethylenediamine core.

Example 3. Preparation of Aqueous Formulation of PAMAM-COOH, PAMAM-Methionine and Exenatide An aqueous formulation is prepared by co-dissolving 4 grams of exenatide, 2 grams of Polymer 2 and 0.5 grams of Polymer 8 in water for injection and bringing the total volume to 10 ml.

The estimated hydrodynamic diameter of exenatide is about 2.4 nm. In order to achieve a constant release rate, the solution is used in combination with a nanopore membrane-controlled drug delivery system with a pore size of 7 nm.

Polymers 2 and 8, based on a $6^{th}$ generation PAMAM have a hydrodynamic radius larger than 7 nm, based on the presence of the carboxylic acid and methionine groups on the PAMAM backbone and will be substantially retained in the drug delivery system during the implantation period.

Example 4. Anti-Microbial Aqueous Formulation of PAMAM-COOH, PAMAM-Methionine, PAMAM-Silver Sulfadiazine and Exenatide The formulation of Example 3 is prepared with the addition of 20 mg of Polymer 10.

Example 5. Solid Formulation of PAMAM-COOH, PAMAM-Tocopherol and Exenatide

A powder mix is prepared of 5 parts exenatide, 5 parts of Polymer 2, and 1 part of Polymer 5. The powder mix can be prepared in any pharmaceutically suitable type of powder mixer. The powder can be filled directly into a reservoir of a drug delivery system, or can be compressed into a pellet and loaded as such in the reservoir.

Example 6. Anti-Microbial Solid Formulation of PAMAM-COOH, PAMAM-Tocopherol, PAMAM-Silver Sulfadiazine and Exenatide The formulation of Example 5 is prepared with the addition of 0.5 parts of Polymer 10.

Example 7. Suspension Formulation of PAMAM-COOH, PAMAM-Tocopherol and Exenatide A suspension formulation can be prepared by suspending the formulation of Example 5 or Example 6 in 11 parts of pharmaceutical grade vegetable oil.

Example 8. Aqueous Formulation of PAMAM-COOH, PAMAM-Methionine and Octreotide An aqueous formulation is prepared by co-dissolving 2 parts of octreotide, 1 part of Polymer 2 and 0.1 part of Polymer 8 in water for injection for a solution with a solid content of 40% w/w.

The estimated hydrodynamic diameter of octreotide is about 1.6 nm. In order to achieve a constant release rate, the solution is used in combination with a nanopore membrane-controlled drug delivery system with a pore size of 5 nm. Polymers 2 and 8, based on a $4^{th}$ generation PAMAM, have a hydrodynamic radius larger than 5 nm, based on the presence of the carboxylic acid and methionine groups on the PAMAM backbone and will be substantially retained in the drug delivery system during the implantation period.

Example 9. Anti-Microbial Aqueous Formulation of PAMAM-COOH, PAMAM-Methionine, PAMAM-Hexachlorophene and Octreotide The formulation of Example 8 is prepared with the addition of 20 mg of Polymer 11.

Example 10. Solid Formulation of PAMAM-COOH, PAMAM-Retinol and Octreotide

A powder mix is prepared of equal parts of octreotide and Polymer 2, with the addition of ⅕ part of Polymer 6. The powder mix can be prepared in any pharmaceutically suitable type of powder mixer. The powder can be filled directly into a reservoir of a drug delivery system, or can be compressed into a pellet and loaded as such in the reservoir.

Example 11. Anti-Microbial Solid Formulation of PAMAM-COOH, PAMAM-Retinol, PAMAM-Silver Sulfadiazine and Octreotide The formulation of Example 10 is prepared with the addition of 0.5 parts of Polymer 10.

Example 12. Suspension Formulation of PAMAM-COOH, PAMAM-Retinol and Octreotide A suspension formulation is prepared by suspending the formulation of Example 10 or Example 11 in 2 parts of pharmaceutical grade vegetable oil.

Example 13. Solid Formulation of PAMAM-Tocopherol and Fluphenazine

A powder mix is prepared of 9 parts fluphenazine and 1 part Polymer 5. The powder mix can be prepared in any pharmaceutically suitable type of powder mixer. The powder can be filled directly into a reservoir of a drug delivery system, or can be compressed into a pellet and loaded as such in the reservoir.

The estimated hydrodynamic diameter of fluphenazine is about 1.4 nm. In order to achieve a constant release rate, the solution is used in combination with a nanopore membrane-controlled drug delivery system with a pore size of 4 nm. Polymer 5, based on a third generation PAMAM has a hydrodynamic radius larger than 4 nm, based on the presence of the tocopherol groups on the PAMAM backbone and will be substantially retained in the drug delivery system during the implantation period.

Example 14. Calculation of Diffusion Rate

According to Fick's Law, Flux F can be expressed as:

$$F = A \times D \times \Delta C \times 1/d$$

wherein
A=Total surface area for diffusion ($cm^2$)
D=Diffusion Coefficient ($cm^2$/sec)
$\Delta C$=Concentration differential (mg/$cm^3$)
d=diffusion path length (cm)
Total surface area for diffusion A is calculated as $$A = N \times \pi \times r^2$$

wherein N=total number of nanopores and r is the radius of the nanopores.

In restricted diffusion through nanopores of appropriate diameter, the dependence of the rate of diffusion on concentration differential disappears, and, instead, the rate of diffusion becomes dependent on the pore diameter. The pore diameter can be controlled by the atomic layer deposition technique described in PCT Publication No. WO 2015/112811, the entirety of which is incorporated herein by reference.

The product of D, $\Delta C$ and ($\pi \times r^2$) can be rewritten as a permeation rate P, in this case with a dimension of mass over time, and unit of mg/sec. The permeation rate P can easily be determined in a traditional membrane—controlled diffusion cell experiment. Consequently, at a fixed nanopore length, the total flux F can now simply and entirely be controlled by the number of nanopores, N.

Diffusion Rate for Exenatide

In one example, for exenatide a delivery rate of 60 µg/day may be desired. In a diffusion cell experiment as mentioned above, a constant release rate profile is measured when using pores of 7 nm, at a rate of $4.5 \times 10^{-12}$ µg/second per nanopore, or $4 \times 10^{-7}$ µg/day per nanopore. In this case, a device with about $1.50 \times 10^8$ nanopores would be sufficient. At a pore density of $3 \times 10^8$ pores/$mm^2$, a window of open nanopores of about 0.5 $mm^2$ will meet the desired release rate profile.

In this example, for a device with a six-month duration of release rate and an efficiency of release of 80%, a payload of about 13 mg exenatide will be adequate. At a packing efficiency of 400 µg of exenatide per microliter of the reservoir of the device, a reservoir of 32.5 microliter will be required. For this application, a device can be designed with an internal reservoir of 2 mm diameter and 11 mm in length. The diameter of 2 mm will accommodate endcaps holding a membrane with an open window area of 0.5 $mm^2$ for the nanopores.

The final formulation in this device would be 13 mg of exenatide, 6.5 mg of Polymer 2, 2.6 mg of Polymer 8 and the remainder water for injection.

Diffusion Rate for Octreotide

In another example, a delivery rate of 160 µg/day may be desired for octreotide. In a diffusion cell experiment as mentioned above, a constant release rate profile is achieved with pores of 5 nm, at a rate of $9 \times 10^{-12}$ µg/second per nanopore, or $8 \times 10^{-7}$ µg/day per nanopore. In this case, a device with about $2 \times 10^8$ nanopores will be sufficient. At a pore density of $3.5 \times 10^8$ pores/mm², a window of open nanopores of about 0.6 mm² will meet the desired release rate profile.

In this example, for a device with a 3-month duration of release rate and an efficiency of release of 80%, a payload of about 17.5 mg octreotide will be adequate. With addition of 17.5 mg of Polymer 2, and about 3.5 mg of Polymer 6, a powder mix of 38.5 mg is obtained. At a powder packing efficiency of 85%, and assuming a powder density of 1.2 g/cm³, a reservoir of 37 microliter will be sufficient.

For this application, a device can be designed with an internal reservoir of 2 mm diameter and 12 mm in length. The diameter of 2 mm will accommodate endcaps holding a membrane with an open window area of 0.6 mm² for the nanopores.

Diffusion Rate for Fluphenazine

In yet another example, for fluphenazine a delivery rate of 2500 µg/day may be desired. In a diffusion cell experiment as mentioned above, a constant release rate profile is achieved with pores of 4 nm, at a rate of $15 \times 10^{-12}$ µg/second per nanopore, or $1.3 \times 10^{-6}$ µg/day per nanopore. In this case, a device with about $2 \times 10^9$ nanopores will be sufficient. At a pore density of $3.5 \times 10^8$ pores/mm², a window of open nanopores of about 6 mm² will meet the desired release rate profile.

In this example, for a device with a 1-month duration of release rate and an efficiency of release of 80%, a payload of about 90 mg fluphenazine will be adequate. Using a powder mix of 9 parts fluphenazine and 1 part Polymer 5, a payload of 100 mg will be required.

At a powder packing efficiency of 85%, and assuming a powder density of 1.2 g/cm³, a reservoir of about 100 microliter will be required. For this application, a device can be designed with an internal reservoir of 3 mm diameter and 15 mm in length. The diameter of 3 mm will accommodate endcaps with the required surface area for the nanopore membranes if both endcaps are used to hold a membrane.

Example 15. Compositions of PAMAM-COOH and Exenatide

The stabilizing capability of dendrimers with acidic end groups in a drug delivery system with a size cut-off membrane was demonstrated with the following example.

Cylindrical titanium reservoirs with an internal volume of 140 microliter were filled with a solution of pure exenatide or with a solution of exenatide with PAMAM-COOH.

The pure exenatide solution contained 20% exenatide in a citrate buffer of pH 4.9. The exenatide solution with PAMAM-COOH was prepared in a similar manner, with the addition of 20% (w/w) PAMAM-COOH. The final pH after addition of the PAMAM-COOH was between 3 and 4.

Both solutions contained 0.02% $NaN_3$ to prevent bacterial growth. The reservoirs were capped with a screw cap holding a dialysis membrane to allow for free exchange of small molecules and ions like protons and citrate buffer between the reservoirs and the incubation liquid, but to retain the PAMAM-COOH in the reservoirs.

The reservoirs were then incubated in phosphate-buffered saline (PBS) at pH 7.4 for 3 months. At the 3 month time point the solutions were analyzed by reverse phase high performance liquid chromatography (RP-HPLC).

The purity of the exenatide in the PAMAM-COOH solutions was still 100% of the initial value by RP-HPLC, while the purity on the exenatide-only solutions had dropped to 83%.

The following calculation demonstrates the use of PAMAM-COOH as a stabilizer in a formulation inside a drug delivery system with a nanoporous membrane having a nominal pore size of 6 nm. In this case, use of a $6^{th}$ generation PAMAM-COOH stabilizer, with a diameter of 6.7 nm, will largely prevent release of the stabilizer through the pores. It should be noted that some escape of the PAMAM-COOH may occur, due to the fact that the pores in the membrane will have a pore size distribution around the nominal pore size of 6 nm.

In order to maintain charge neutrality, the loss of a proton needs to be compensated by uptake of another cation, in an environment of actual use most likely a sodium ion. Consequently, the loss of a proton essentially represents the neutralization of an acid group on a polymer. The effects of sodium ion transport have not been taken into account in this example.

Using Fick's Law for the calculation of Flux F, described above, calculation shows the rate of diffusion of acidic protons out of a device under the following conditions:

Calculation of total surface area for diffusion, A. The drug delivery system in this example has a membrane with 132 million nanotubes with a diameter of 6 nm, or $6 \times 10^{-7}$ cm. Accordingly, the total surface area for diffusion can be calculated as:

$$A = 132 \times 10^6 \times \pi \times (3 \times 10^{-7})^2 = 4 \times 10^{-5} \text{ cm}^2$$

Calculation of concentration differential, $\Delta C$. When using as internal pH of 4, and an external pH of 7, the concentration differential can be written as:

$$\Delta C = (10^{-4} \text{ mmole/cm}^3 - 10^{-7} \text{ mmole/cm}^3) \approx 10^{-4} \text{ mmole/cm}^3$$

Proton diffusion coefficient, D, is $10^{-4}$ cm²/sec, based on literature data.

Diffusion path length, d, is the nanotube length, which can be 50 micrometer, $50 \times 10^{-4}$ cm.

Based on the above, and on the assumption of strictly Fickian diffusion control, the loss rate of protons through the membrane is $8 \times 10^{-11}$ mmole/second, equivalent to $7 \times 10^{-6}$ mmole/day.

In the case of PAMAM-COOH, there are 256 end groups on a $6^{th}$ generation PAMAM backbone of 58,025 Da, so a weight equivalence of about 226 Da per acid group. Consequently, the rate of proton loss is equivalent to the loss of $7 \times 10^{-6} \times 226$ mg, or about 1.6 micrograms of PAMAM-COOH acid carrying capacity per day.

Example 16. Determination of Exenatide Purity

The following example provides a procedure for determining the purity of exenatide released by an implantable drug delivery system of the present invention.

Exenatide purity can be determined using HPLC under the following conditions:
HPLC Mobile Phase:
    Mobile Phase A (0.1% TFA in Water):
    Add 1 mL of trifluoroacetic acid to 1 L of water.
    Mobile Phase B (0.1% TFA in Acetonitrile):
    Add 1 mL of trifluoroacetic acid to 1 L of acetonitrile.
Standards:
    Exenatide Stock Solution (1.0 mg/mL):
    Add 1.40 mg of Exenatide to 1400 µL of water Standard 7 (100 μg/mL):
Add 200 μL of Exenatide stock solution (1.0 mg/mL) to 1800 μL of water.
Make a serial dilution of Standard 7 (100 μg/mL) with water to 0.5, 1, 2.5, 5, 10, 50, and 100 μg/mL.

| Table of HPLC Conditions | |
|---|---|
| Column | Vydac, Protein C4, 3.2 mm xl 50 mm, 5 μm |
| Mobile Phase A | 0.1% TFA in Water |
| Mobile Phase B | 0.1% TFA in Acetonitrile |
| Column Temperature | Ambient |
| Autosampler Temperature | 4° C. |
| Flow rate | 0.75 mL/min |
| Injection volume | 25 μL |
| Detector wavelength | 220 nm |

| | Time (min) | Mobile Phase B (%) |
|---|---|---|
| Gradient | 0 | 25 |
| | 20 | 60 |
| | 20.1 | 25 |
| | 28 | 25 |
| Run time | 28 minutes | |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. An implantable drug delivery system, said implantable drug delivery system comprising:
   a capsule suitable for implantation;
   a reservoir encapsulated by the capsule:
   a membrane in contact with the reservoir, wherein the reservoir contains a pharmaceutical composition of a therapeutic agent, which therapeutic agent is a peptide, together with a polymeric stabilizing agent comprising a polymer having a plurality of stabilizing groups, wherein the polymer is a dendritic polymer or is a cross-linked polymer;
   said capsule having a nanoporous membrane with a plurality of pores;
   said plurality of stabilizing groups having molecular dimensions larger than the pore size of the nanoporous membrane; and wherein the release of said polymeric stabilizing agent from the reservoir is substantially prevented.

2. The delivery system of claim 1, wherein the therapeutic agent is selected from the group consisting of beta-glucocerobrosidase, interferon alpha, interferon beta, agasidase alpha, agasidase beta, exenatide, nutropin/somatropin, factor VIII, fondaparinux, aldesleukinand, risperidone, forigerimod, NP fusion proteins, IL-12, a melanocyte stimulating hormone, and bapineuzumab.

3. The delivery system of claim 2, wherein the therapeutic agent is selected from the group consisting of exenatide, octreotide and fluphenazine.

4. The delivery system of claim 2, wherein the therapeutic agent comprises exenatide.

5. The delivery system of claim 1, wherein the polymer is a dendritic polymer.

6. The delivery system of claim 1, wherein the polymer is a poly(amidoamine) dendrimer having a plurality of end groups, wherein the plurality of end groups comprise at least one member selected from the group consisting of the acid groups, the base groups, alkyl, hydroxyalkyl, amidoethanol, amidoethylethanolamine, ethylenediamine, sodium carboxylate, succinamic acid, trimethoxysilyl, tris(hydroxymethyl)amidomethane, and 3-carbomethoxypyrrolidinone.

7. The delivery system of claim 6, wherein the end groups of the poly(amidoamine) dendrimer comprise sodium carboxylate.

8. The delivery system of claim 1, wherein each stabilizing group is independently selected from the group consisting of an acid group, a base group, an anti-oxidant, an anti-microbial, an anti-biotic, a protein clustering agent, and a protein declustering agent.

9. The delivery system of claim 1, wherein each stabilizing group is independently selected from the group consisting of an acid group and a base group.

10. The delivery system of claim 9, wherein the acid groups are selected from the group consisting of carboxylic acid, amino acid, thiol, and phenol.

11. The delivery system of claim 9, wherein the base groups are selected from the group consisting of hydroxy, cyano, amine and carboxylate.

12. The delivery system of claim 1, wherein the polymer is crossed-linked.

13. The delivery system of claim 1, wherein the polymer is co-polymer.

14. The delivery system of claim 1, wherein the polymer is polyacrylic acid.

15. The delivery system of claim 1, wherein the polymer is polymethacrylic acid.

16. The delivery system of claim 14, wherein the polymer is co-polymer.

17. The delivery system of claim 15, wherein the polymer is co-polymer.

18. The delivery system of claim 1, wherein the implantable drug delivery device contains a second nanoporous membrane.

19. The delivery system of claim 18, wherein the second membrane provides a diffusion pathway for the therapeutic agent.

20. The delivery system of claim 1, wherein the pH of the composition is from about 3 to 7.

21. An implantable drug delivery system, said implantable drug delivery system comprising:
   a capsule having a nanoporous membrane with a plurality of pores, the capsule configured for implantation;
   a reservoir encapsulated by the capsule, the reservoir containing a pharmaceutical composition, said pharmaceutical composition comprising:
   a therapeutic agent, which therapeutic agent is a peptide, together with a polymeric stabilizing agent comprising a polymer having a plurality of stabilizing groups, wherein the polymer is a dendritic polymer or is a cross-linked polymer;
   the polymeric stabilizing agent comprising a polymer having a plurality of stabilizing groups having molecular dimensions larger than the pore size of the nanoporous membrane, wherein the release of the polymeric stabilizing agent from the reservoir is substantially prevented; and wherein the nanoporous membrane is a diffusion pathway out of the reservoir for the therapeutic agent.

22. The delivery system of claim 21, wherein the therapeutic agent is selected from the group consisting of exenatide, octreotide and fluphenazine.

23. The delivery system of claim 21, wherein the therapeutic agent comprises exenatide.

24. The delivery system of claim 21, wherein the polymer is crossed-linked.

25. The delivery system of claim 21, wherein the polymer is co-polymer.

26. The delivery system of claim 21, wherein the polymer is polyacrylic acid.

27. The delivery system of claim 21, wherein the polymer is polymethacrylic acid.

28. The delivery system of claim 26, wherein the polymer is co-polymer.

29. The delivery system of claim 27, wherein the polymer is co-polymer.

\* \* \* \* \*